United States Patent [19]

Hinchliffe et al.

[11] Patent Number: 5,707,380
[45] Date of Patent: Jan. 13, 1998

[54] ANASTOMOSIS INSTRUMENT AND METHOD

[75] Inventors: Peter W.J. Hinchliffe, New Haven; Keith Ratcliff, Newtown; Scott E. Manzo, Shelton; David T. Green, Westport, all of Conn.

[73] Assignee: United States Surgical Corporation, Norwalk, Conn.

[21] Appl. No.: 685,385

[22] Filed: Jul. 23, 1996

[51] Int. Cl.⁶ .................................................. A61B 17/04
[52] U.S. Cl. .................................................. 606/153
[58] Field of Search ............................ 606/142, 143, 606/151, 153, 154; 227/19

[56] References Cited

U.S. PATENT DOCUMENTS

| | | |
|---|---|---|
| D. 276,650 | 12/1984 | Green et al. . |
| 2,968,041 | 1/1961 | Skold .................. 606/142 |
| 3,152,336 | 10/1964 | Brady .................. 606/142 |
| 3,232,089 | 2/1966 | Samuels et al. . |
| 3,366,301 | 1/1968 | Mallina ................ 606/153 |
| 3,519,187 | 7/1970 | Kapitanov et al. . |
| 3,575,038 | 4/1971 | Mallet . |
| 3,856,016 | 12/1974 | Davis .................. 606/151 |
| 3,954,108 | 5/1976 | Davis .................. 606/142 |
| 4,152,920 | 5/1979 | Green .................. 606/142 |
| 4,166,466 | 9/1979 | Jarvik . |
| 4,201,314 | 5/1980 | Samuels et al. ........ 221/198 |
| 4,242,902 | 1/1981 | Green .................. 606/142 |
| 4,266,242 | 5/1981 | Jarvik .................. 606/142 |
| 4,299,224 | 11/1981 | Noiles ................. 606/142 |
| 4,316,468 | 2/1982 | Klieman et al. ....... 606/143 |
| 4,325,376 | 4/1982 | Klieman et al. . |
| 4,350,160 | 9/1982 | Kolesov et al. . |
| 4,368,736 | 1/1983 | Kaster ................. 606/143 |
| 4,372,316 | 2/1983 | Blake, III et al. . |
| 4,408,603 | 10/1983 | Blake, III et al. . |
| 4,412,539 | 11/1983 | Jarvik . |
| 4,425,915 | 1/1984 | Ivanov . |
| 4,430,997 | 2/1984 | DiGiovanni et al. . |
| 4,452,376 | 6/1984 | Klieman et al. . |
| 4,466,436 | 8/1984 | Lee . |
| 4,480,640 | 11/1984 | Becht . |
| 4,509,518 | 4/1985 | McGarry et al. . |
| 4,522,207 | 6/1985 | Klieman et al. . |
| 4,532,925 | 8/1985 | Blake, III . |
| 4,534,351 | 8/1985 | Rothfuss et al. . |
| 4,586,503 | 5/1986 | Kirsch et al. . |
| 4,598,711 | 7/1986 | Deniega . |
| 4,611,595 | 9/1986 | Klieman et al. . |
| 4,616,650 | 10/1986 | Green et al. . |
| 4,712,549 | 12/1987 | Peters et al. . |
| 4,733,664 | 3/1988 | Kirsch et al. . |
| 4,759,364 | 7/1988 | Boebel . |
| 4,809,695 | 3/1989 | Gwathmey et al. . |
| 4,821,939 | 4/1989 | Green . |
| 4,929,240 | 5/1990 | Kirsch et al. . |

(List continued on next page.)

FOREIGN PATENT DOCUMENTS

| | | |
|---|---|---|
| 0594004 | 4/1994 | European Pat. Off. . |
| 0656191 | 6/1995 | European Pat. Off. . |
| 8801486 | 8/1987 | WIPO . |
| 9535065 | 5/1995 | WIPO . |

OTHER PUBLICATIONS

LIGACLIP Ligating Clips and Appliers Brochure; 1982 Ehticon, Inc.

Hemoclip Automatic Ligating Clip System Advertisement; Sep. 1986, Surgery, Gynecology & Obstetrics.

*Primary Examiner*—Gary Jackson

[57] ABSTRACT

A surgical instrument for anastomosis of first and second blood vessels is provided having a handle and a body portion extending distally from the handle. A fastener support is mounted adjacent a distal end portion of the body portion. A plurality of surgical fasteners are releasably supported by the fastener support at the distal end thereof. The surgical fasteners each have a leg with an atraumatic tip. A fastener camming member is mounted adjacent the fastener support. The fastener camming member and fastener support are relatively slidable in response to actuation of the handle to simultaneously deform the surgical fasteners to secure the first and second vessels without piercing the vessels.

22 Claims, 16 Drawing Sheets

U.S. PATENT DOCUMENTS

| | | |
|---|---|---|
| 4,930,674 | 6/1990 | Barak . |
| 4,979,954 | 12/1990 | Gwathmey et al. . |
| 4,983,176 | 1/1991 | Cushman et al. . |
| 5,030,226 | 7/1991 | Green et al. . |
| 5,104,395 | 4/1992 | Thornton et al. . |
| 5,112,343 | 5/1992 | Thornton . |
| 5,122,150 | 6/1992 | Puig . |
| 5,188,638 | 2/1993 | Tzakis ................................ 606/153 |
| 5,192,288 | 3/1993 | Thompson et al. . |
| 5,234,447 | 8/1993 | Kaster et al. . |
| 5,314,436 | 5/1994 | Wilk ........................................ 606/153 |
| 5,340,360 | 8/1994 | Stefanchik . |
| 5,346,115 | 9/1994 | Perouse et al. . |
| 5,354,304 | 10/1994 | Allen et al. . |
| 5,366,462 | 11/1994 | Kaster et al. . |
| 5,403,333 | 4/1995 | Kaster et al. . |
| 5,431,668 | 7/1995 | Burbank, III et al. . |
| 5,443,198 | 8/1995 | Viola et al. . |
| 5,486,187 | 1/1996 | Schenck . |
| 5,501,698 | 3/1996 | Roth et al. . |

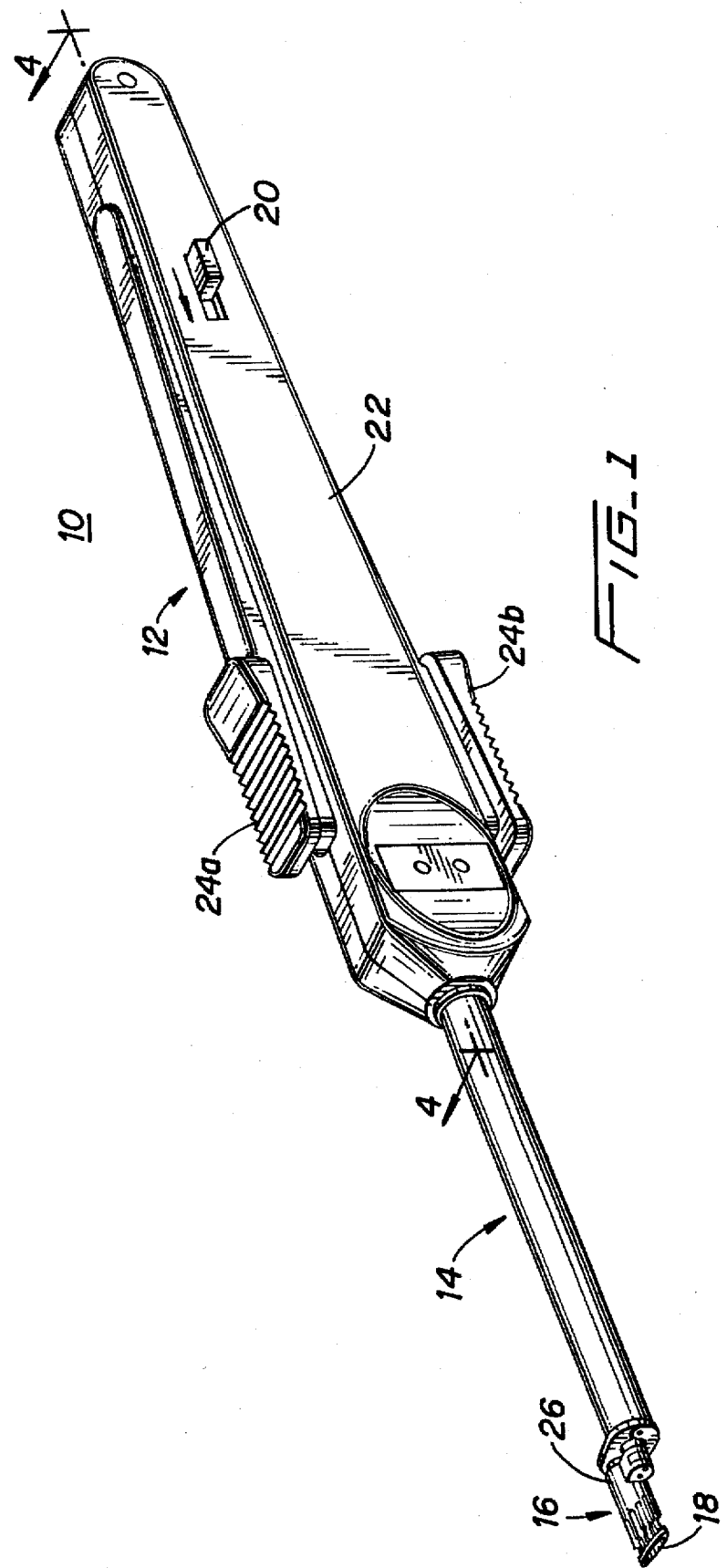

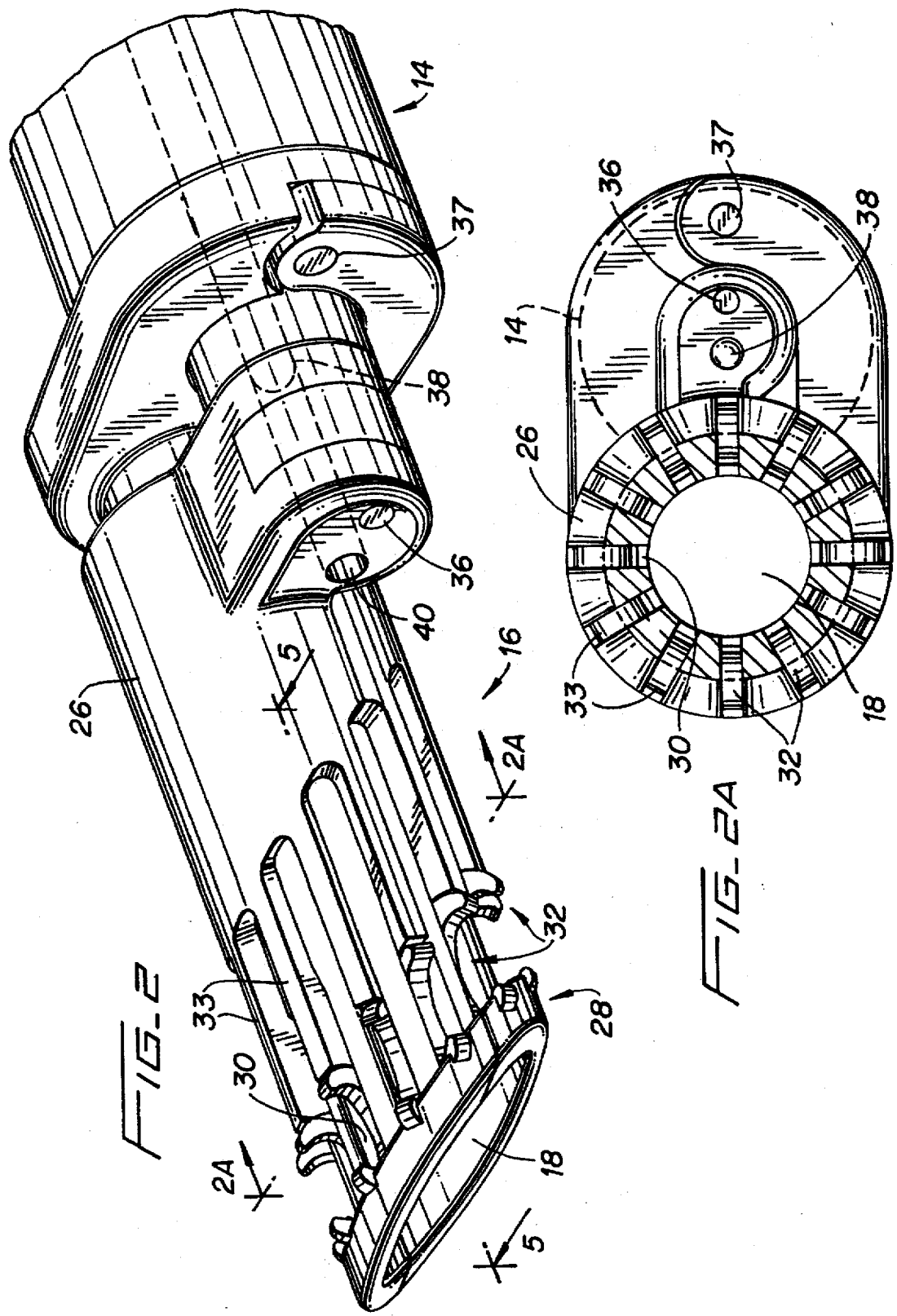

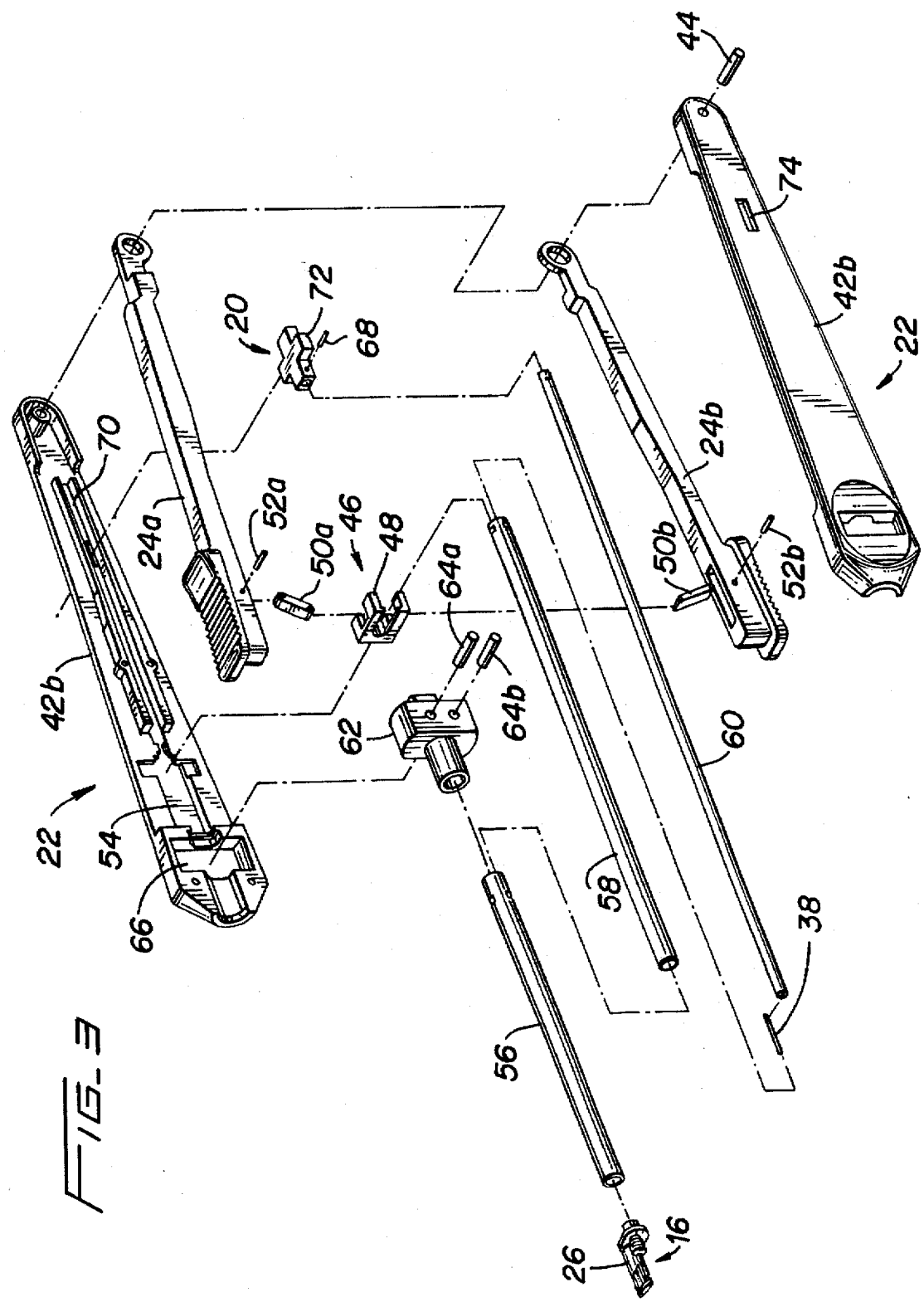

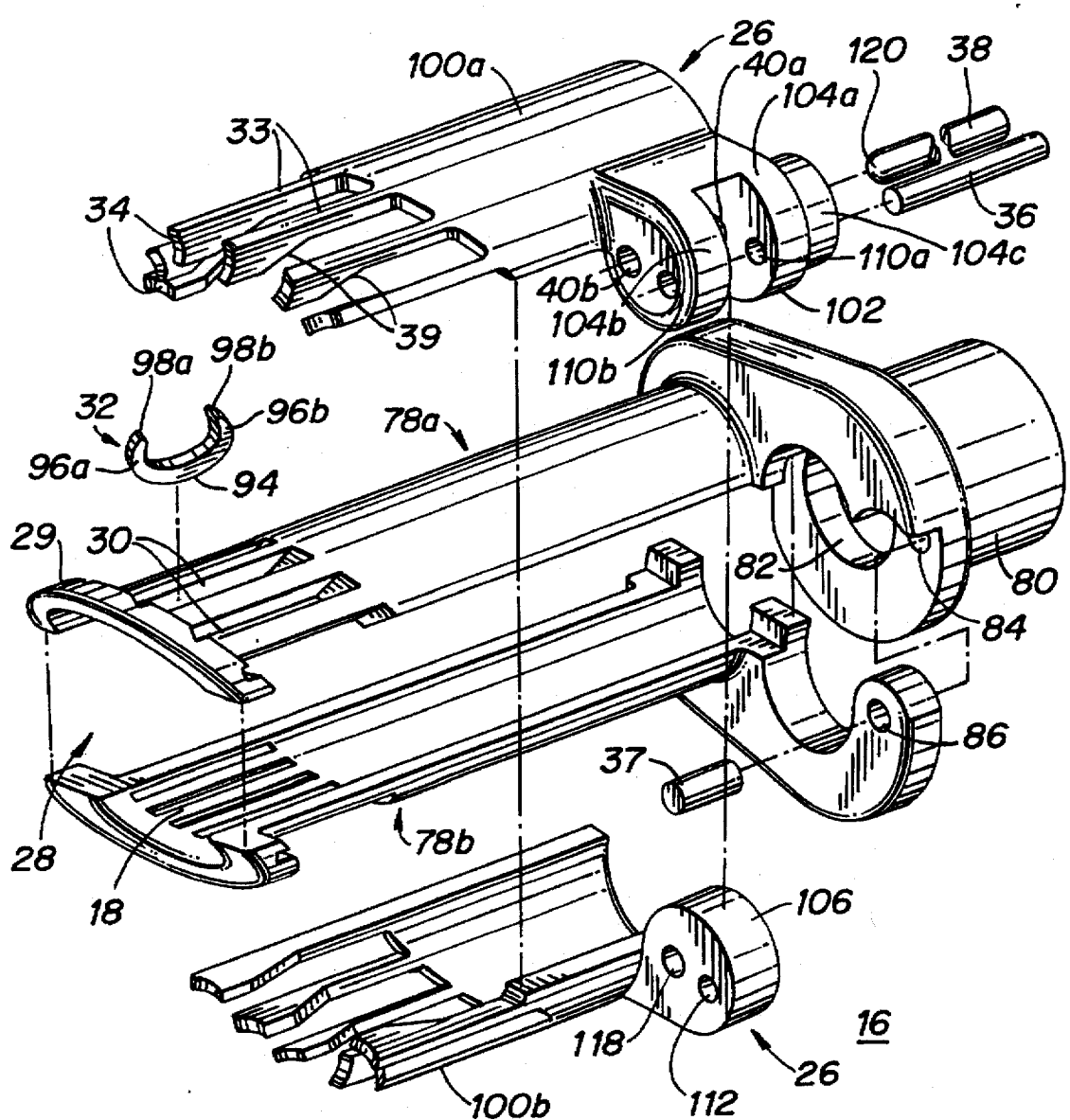

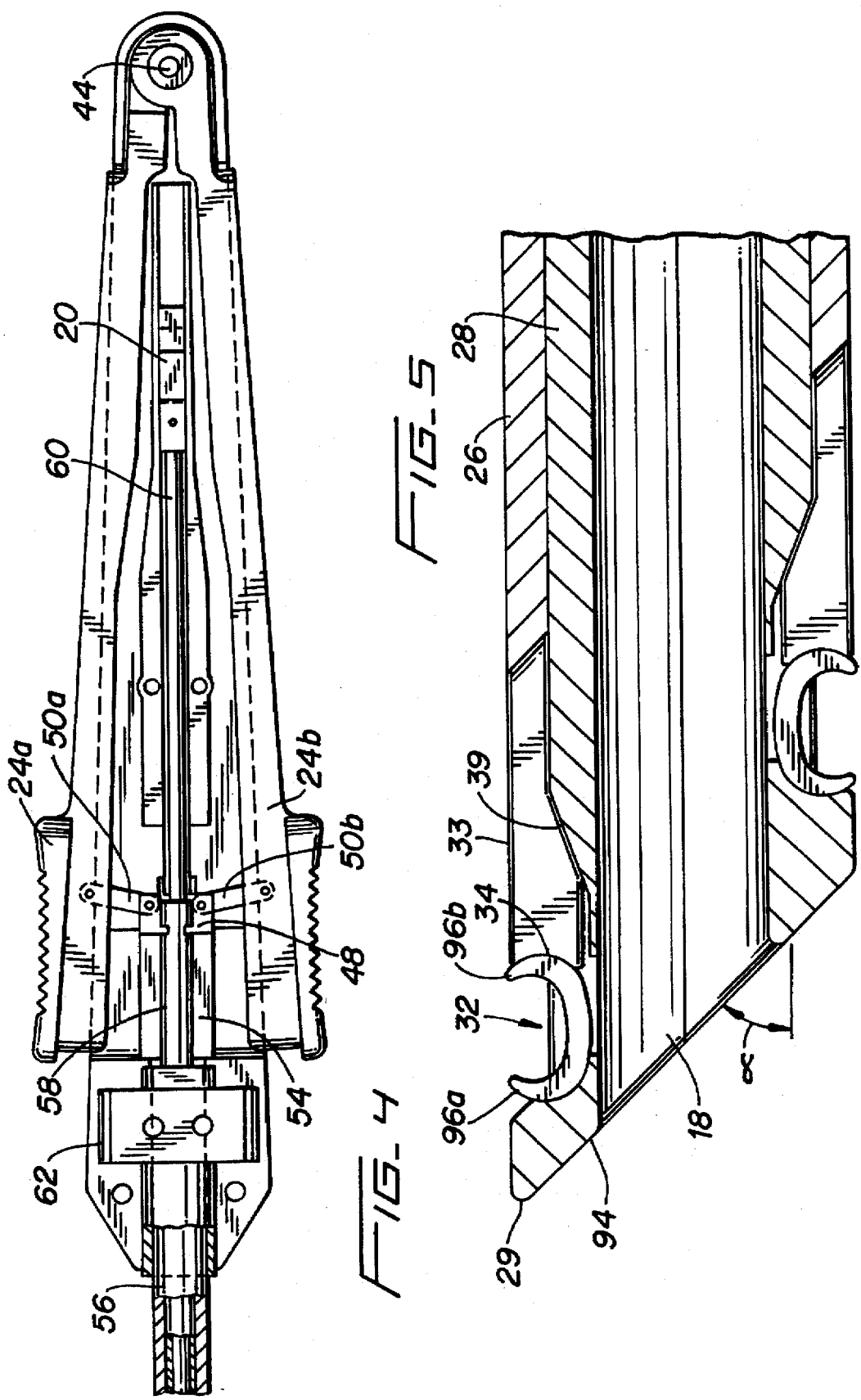

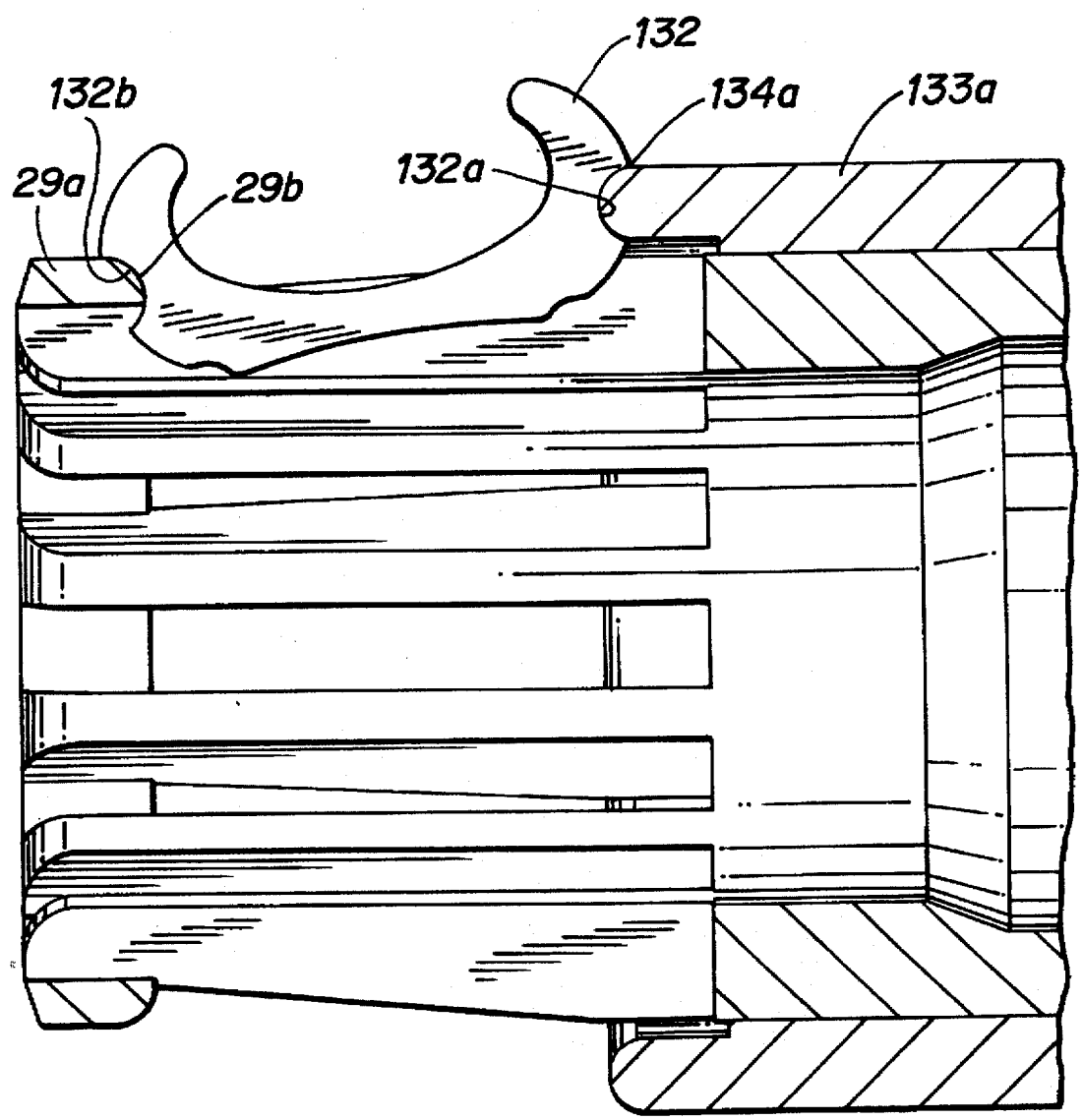
FIG_5A

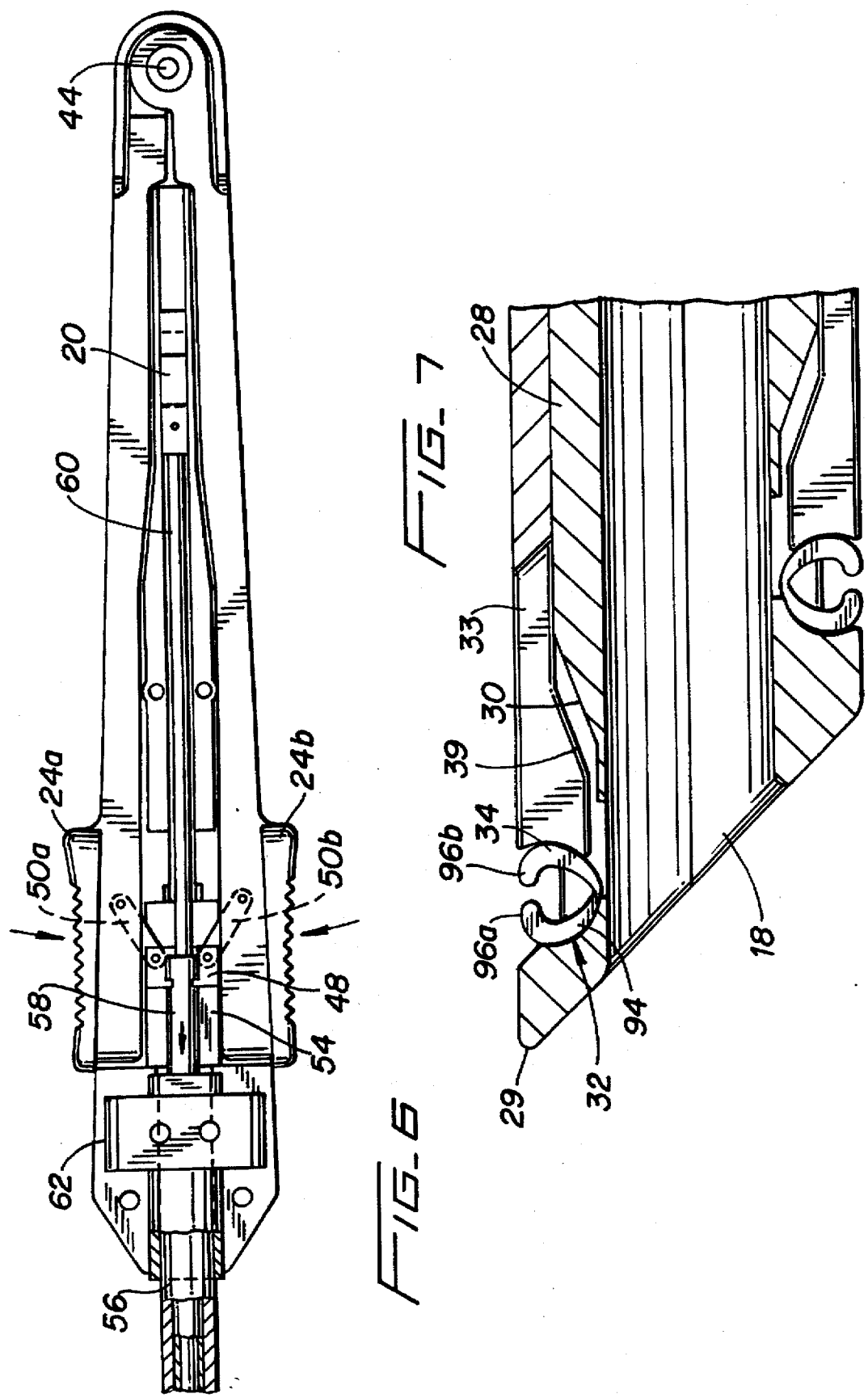

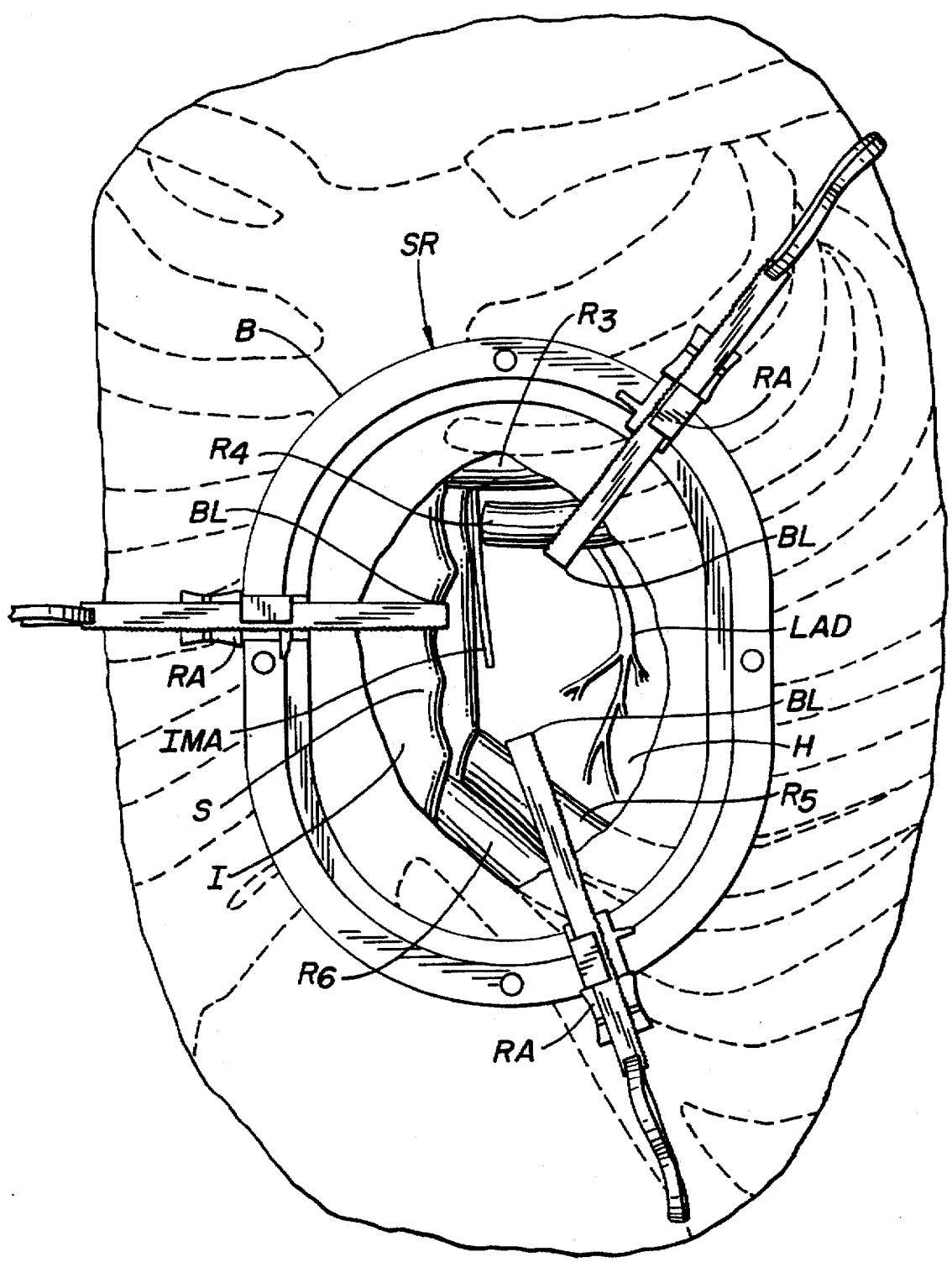

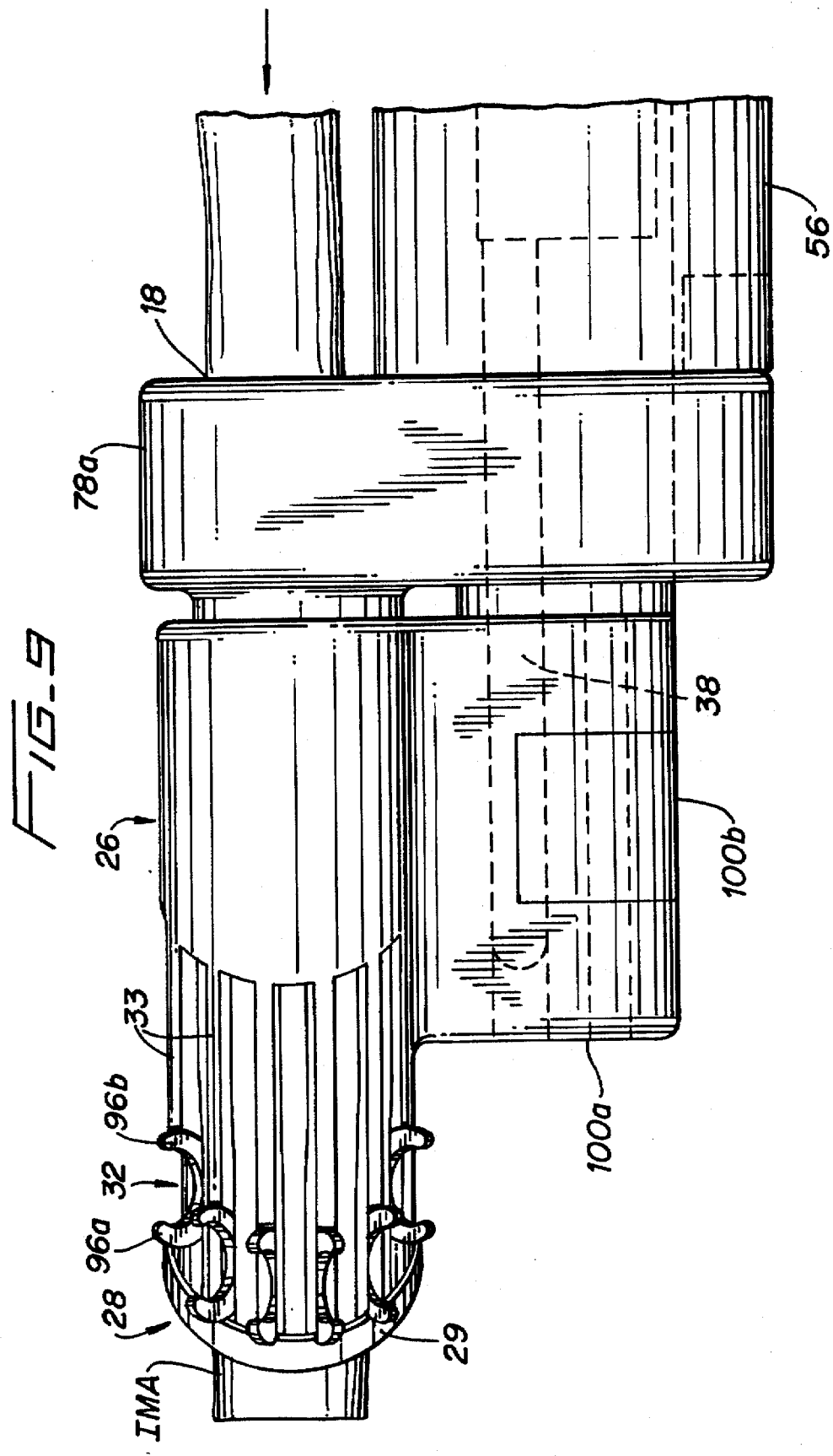

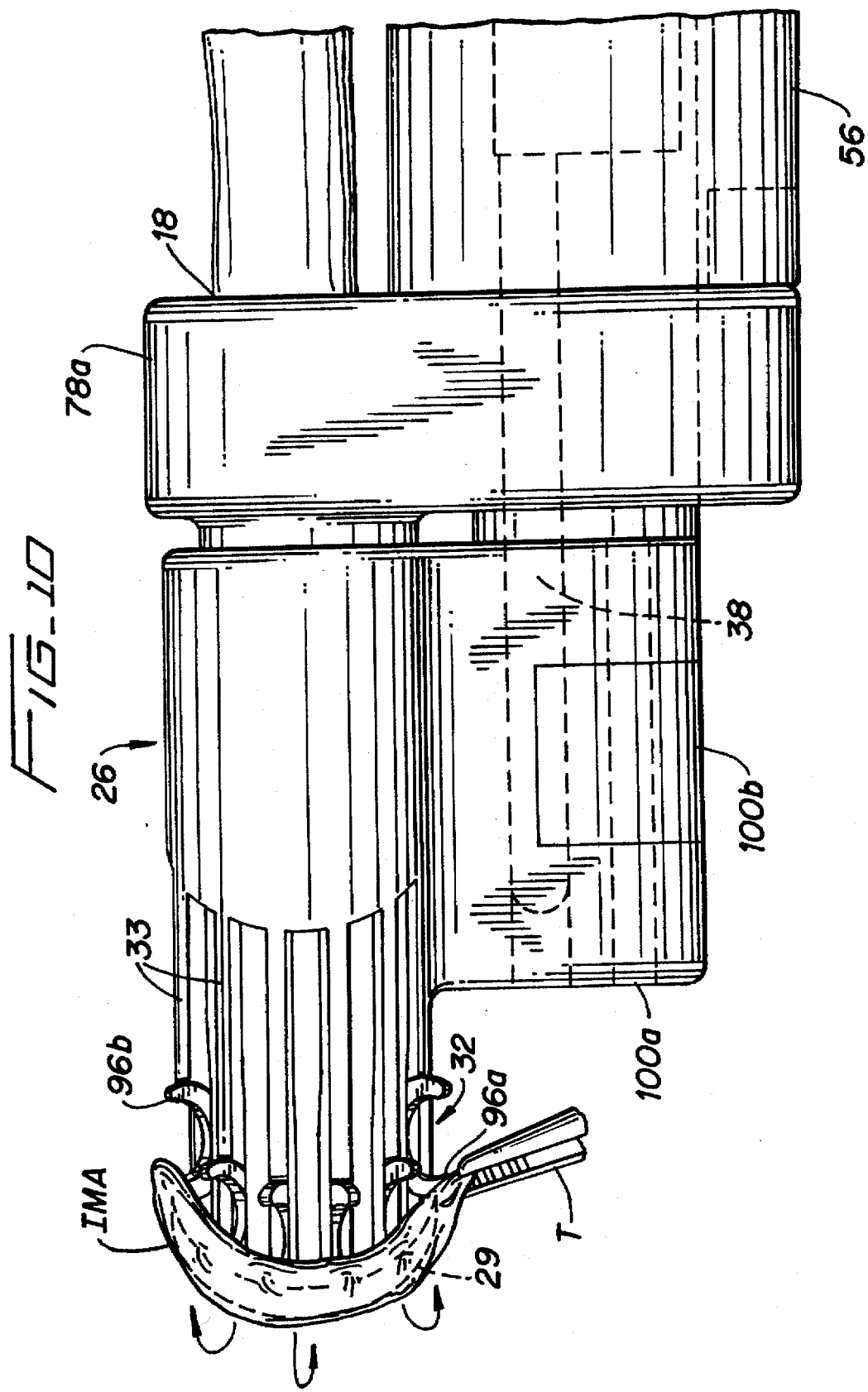

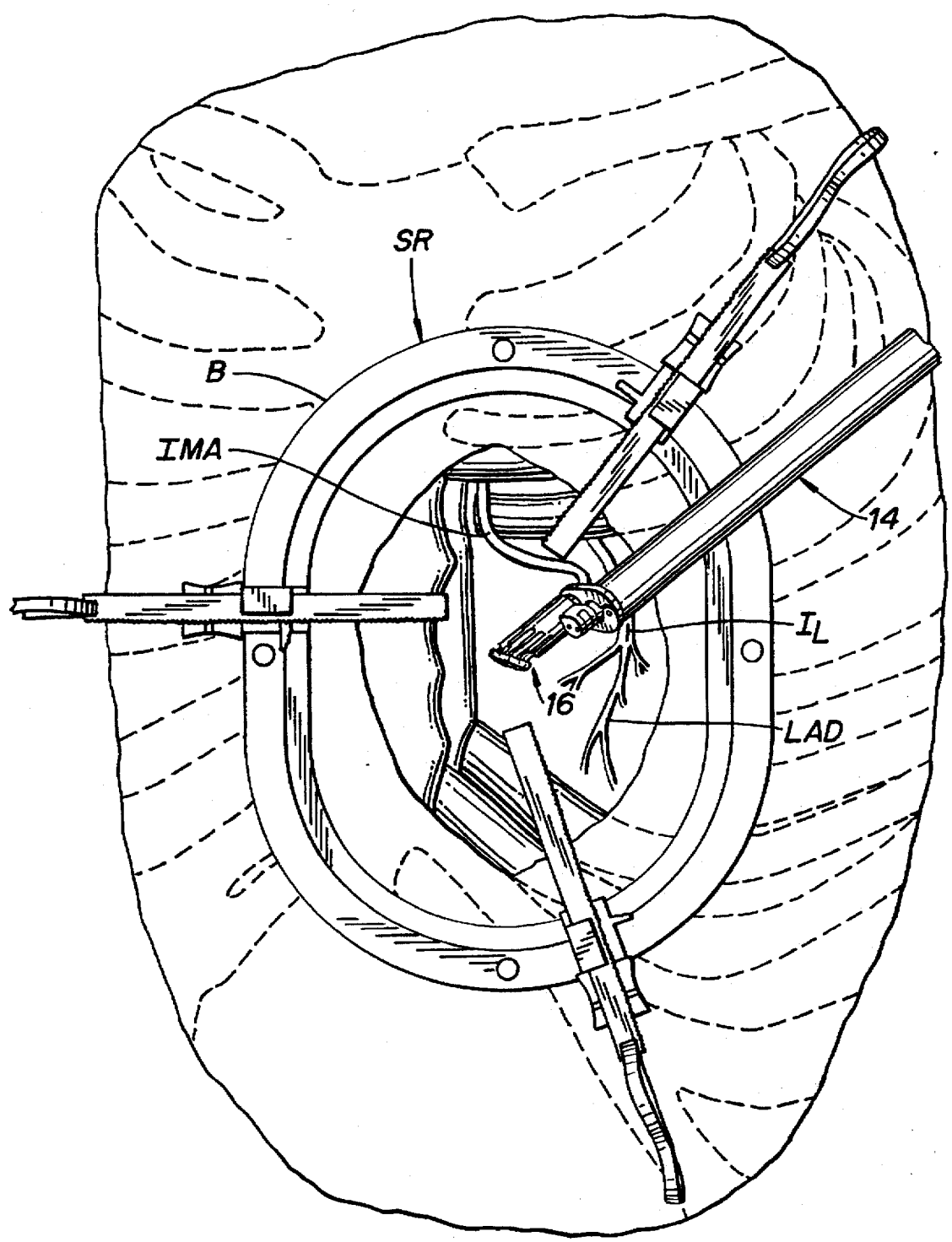
FIG_11

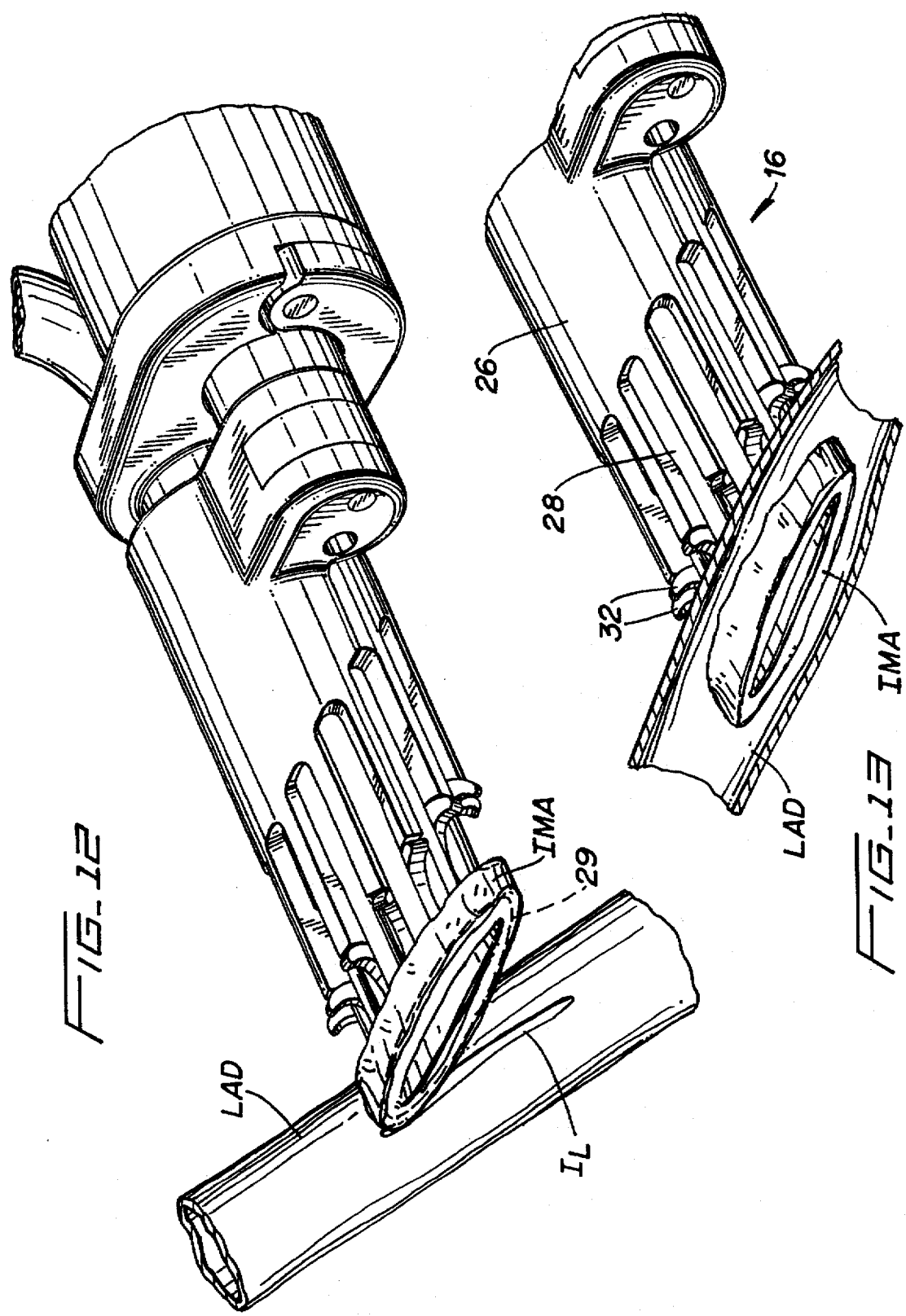

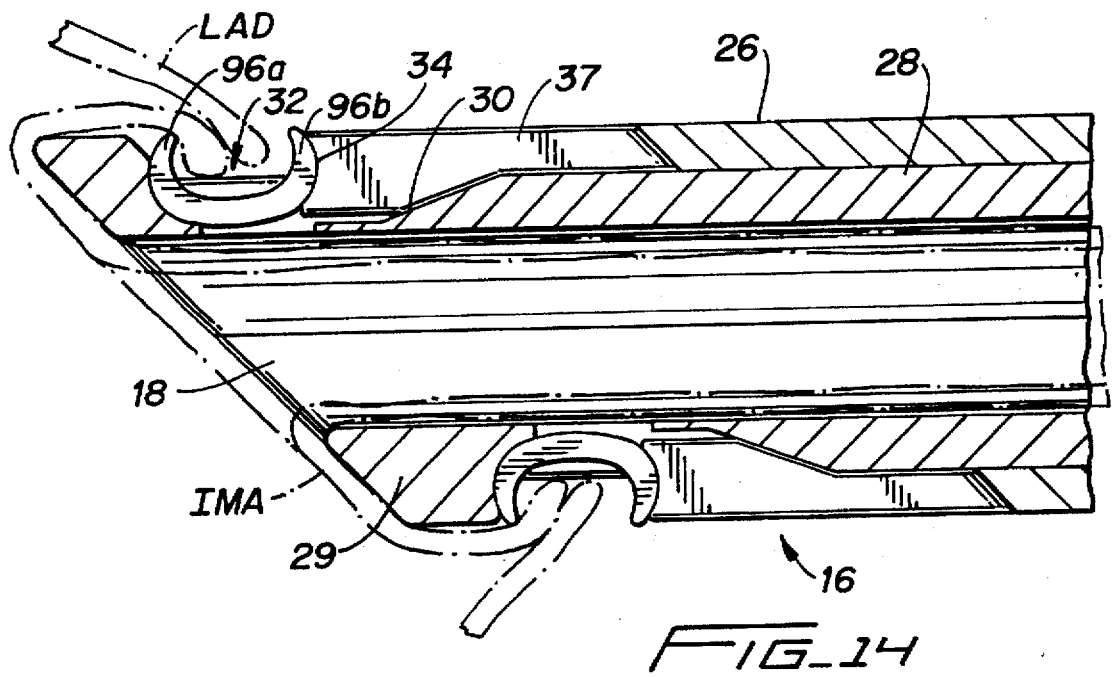
FIG_14
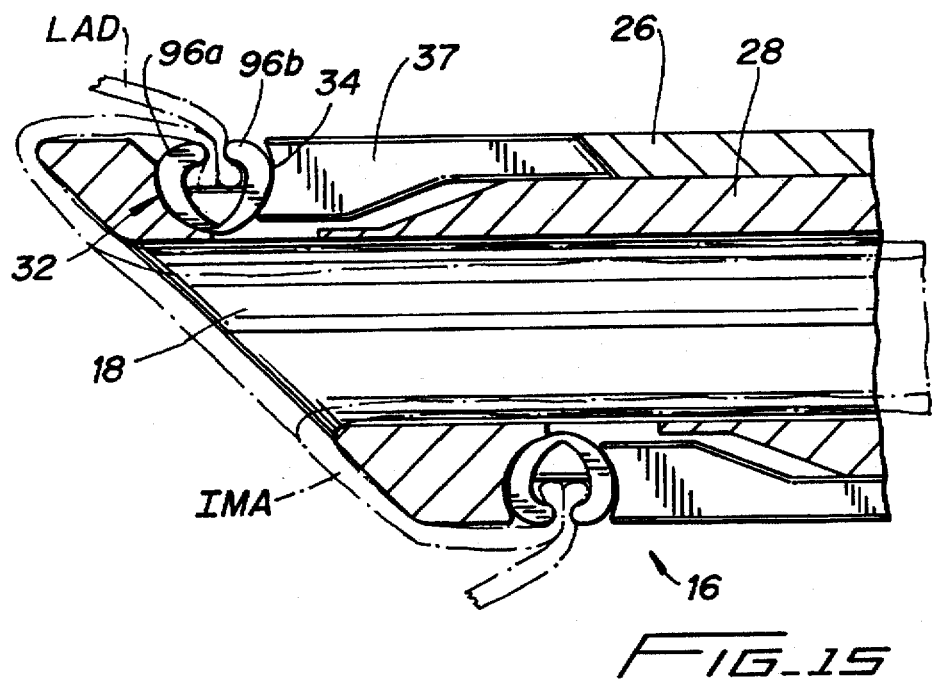
FIG_15

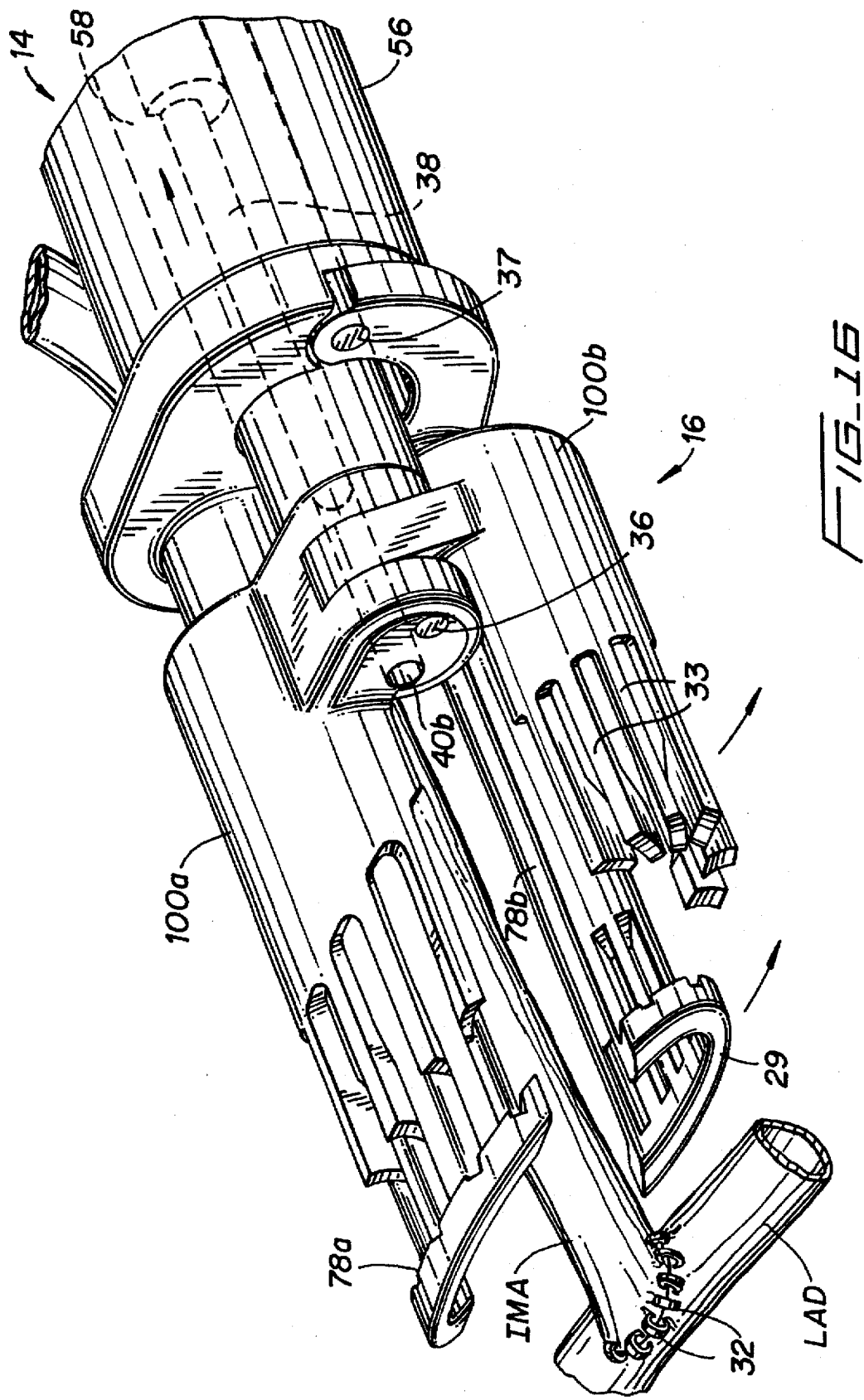

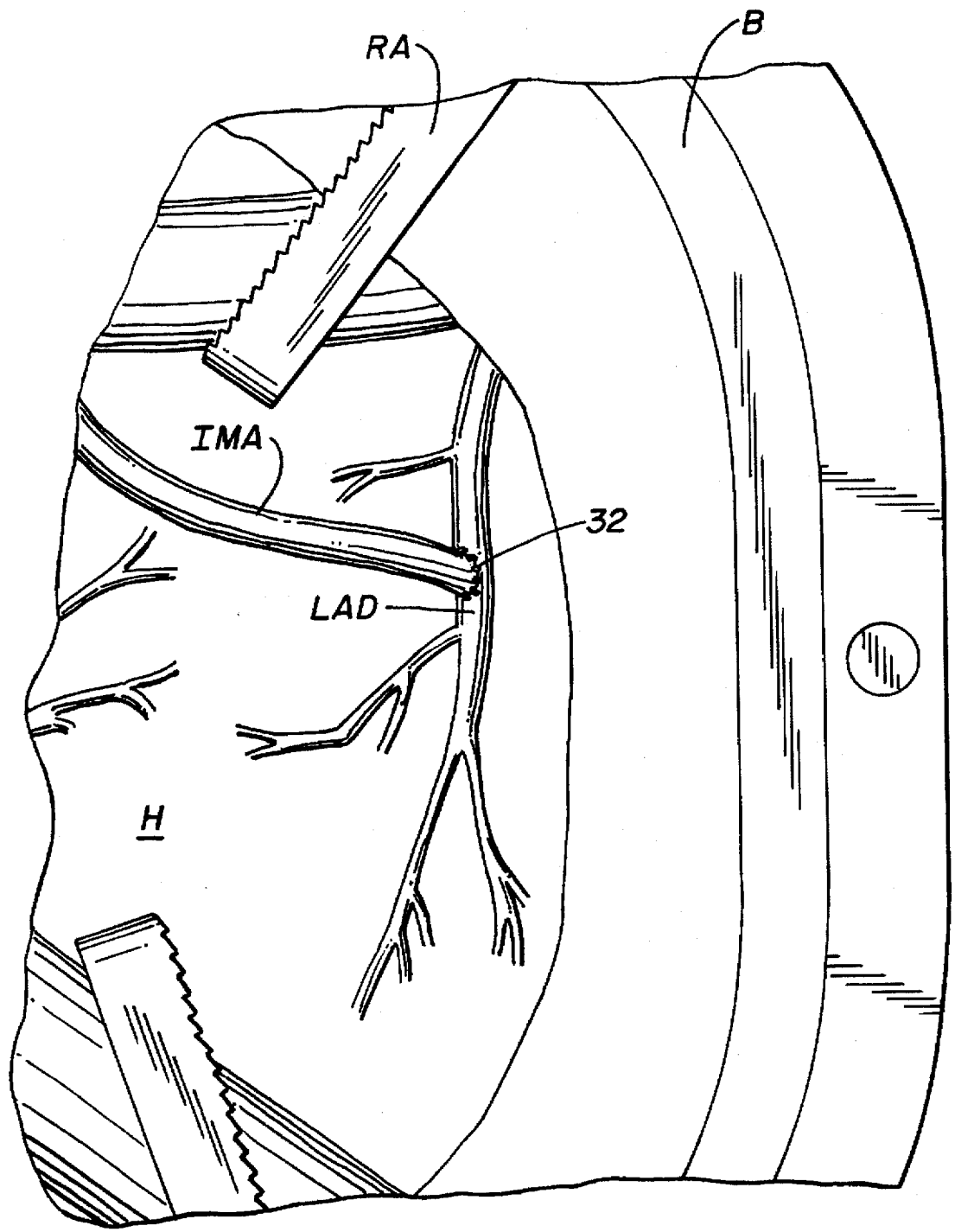
FIG_17

ANASTOMOSIS INSTRUMENT AND METHOD

BACKGROUND

1. Technical Field

The subject disclosure relates to a surgical apparatus and method for performing anastomosis of tubular body structures, and more particularly to an instrument for joining vascular tissues.

2. Background of Related Art

Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and by modifications in behavior and diet. In other cases, dilatation of coronary arteries may be achieved by such procedures as angioplasty, laser ablation, atherectomy, catheterization, and intravascular stents.

For certain patients, coronary artery bypass grafting (CABG) is the preferred form of treatment to relieve symptoms and often increase life expectancy. CABG consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery (IMA) is located in the thoracic cavity adjacent the sternum and is likewise suitable for grafting to a coronary artery, such as the left anterior descending artery (LAD).

The performance of CABG typically requires access to the heart, blood vessels and associated tissue. Access to the patient's thoracic cavity may be achieved in an open procedure by making a large longitudinal incision in the chest. This procedure, referred to as a median sternotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating window. The retractor includes a rigid frame and a translation frame slidably connected to the rigid frame. Lower and upper blades are rotatably mounted to the rigid frame and the translation frame respectively. The window approach enables the surgeon to gain access through a smaller incision and with less displacement of the ribs, and consequently, less trauma to the patient.

Once access to the thoracic cavity has been achieved, surgery on the heart may be performed. Such procedures typically require that the heart beat be arrested while maintaining circulation throughout the rest of the body. Cardioplegic fluid, such as potassium chloride (KCl) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta. Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is complicated procedure requiring that the desired vessels be properly located and accessed. The progression of the guide wires and catheters must be closely monitored to determine proper placement. Furthermore, the introduction of catheters forms punctures in the blood vessels that must be subsequently closed, and there is an increased risk of trauma to the interior walls of the vessels in which the catheters must pass.

Alteratively, the CABG procedure may be performed while the heart is permitted to beat. A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform the CABG procedure, the harvested vessel segment, such as the IMA, is grafted to the coronary artery by end-to-side anastomosis. Typically, sutures are used to graft the vessel segments. However, conventional suturing is complicated by the use of minimally invasive procedures, such as the window approach. Limited access and reduced visibility may impede the surgeon's ability to manually apply sutures to a graft. Additionally, it is difficult and time consuming to manually suture if the CABG procedure is being performed while the heart is beating as the suturing must be synchronized with the heart beat.

The process of manually suturing the harvested vessel segment to a coronary artery is time consuming and requires a great deal of skill on the part of the surgeon. The resulting sutured anastomosis will also be dependent on the skills of the surgeon. In minimally invasive procedures, the ability to suture is even more complicated due to limited maneuverability and reduced visibility. Therefore, a need exists for an apparatus and a procedure that enables the remote anastomosis without piercing fire vessels during both conventional and minimally invasive procedures in a consistent and rapid manner.

SUMMARY

The present disclosure is directed to an instrument for anastomosis of first and second blood vessels. The instrument has a handle and a body portion extending distally from the handle. A fastener support or anvil is mounted adjacent a distal end portion of the body portion. A plurality of surgical fasteners are releasably supported by the anvil and radially oriented about the distal end thereof. Each surgical fastener has a leg with an atraumatic tip portion. A fastener camming member or fastener pusher is mounted adjacent the fastener support member. The fastener support and fastener camming member are relatively slidable in response to actuation of the handle to simultaneously deform the surgical fasteners to secure a first and second vessel without piercing the vessels.

In a preferred embodiment the fastener support defines a passage therethrough. The passage is preferably laterally offset from the body portion. The fastener support defines a longitudinal axis and has a distal end angularly disposed with respect to the longitudinal axis. The fastener support and the fastener pusher may each be composed of at least two separable components. The components of the fastener camming may be secured together by a lock which is remotely actuated adjacent the handle.

A method for anastomosis of first and second blood vessels is also disclosed. The method includes providing a surgical instrument having a fastener support member defining a passage therethrough for reception of a first vessel. A plurality of surgical fasteners, each having at least one leg with an atraumatic tip portion, are provided which are releasably supported by the fastener support member at a distal end thereof. A fastener pusher or camming member is provided which is mounted adjacent the fastener support, and the fastener camming and the fastener support are relatively slidable in response to actuation of the handle to simultaneously deform a leg of each of the surgical fasteners.

The method further includes positioning an end of the first vessel through the passage and everting the vessel over a distal end of the fastener support member adjacent the plurality of surgical fasteners. The first vessel is then engaged with each of the surgical fasteners. The distal end of the fastener support member is inserted to mount the end of the first vessel into an opening in the second vessel. The surgical fasteners engage the side wall of the second vessel adjacent the opening. A leg of the surgical fasteners is simultaneously deformed to secure the first and second vessels together without piercing the vessels.

The first vessel is then released from the fastener support member. In a preferred embodiment, the fastener support and the fastener pusher are each composed of at least two separable elements, and the step of releasing the first vessel includes separating the components of the fastener support and of the fastener pusher. The surgical instrument is sized and configured to be percutaneously inserted to the operative site adjacent the first and second blood vessels.

These and other features of the surgical instrument will become more readily apparent to those skilled in the art from the following detailed description of preferred embodiments of the subject disclosure.

BRIEF DESCRIPTION OF THE DRAWINGS

Various embodiments of the subject surgical apparatus and method are described herein with reference to the drawings wherein:

FIG. 1 is a perspective view of a surgical instrument constructed in accordance with a preferred embodiment of the subject disclosure;

FIG. 2 is an enlarged perspective view of the surgical instrument of FIG. 1, illustrating the anvil assembly in a closed, unlocked configuration;

FIG. 2A is an enlarged cross-sectional view of the anvil assembly;

FIG. 3 is a perspective view with parts separated of the surgical instrument;

FIG. 3A is an enlarged perspective view with parts separated of the anvil assembly;

FIG. 4 is a cross-sectional view of the handle assembly taken along line 4—4 of FIG. 1, illustrating the levers in a spaced apart configuration;

FIG. 5 is an enlarged cross-sectional view of the anvil assembly taken along line 5—5 of FIG. 2, illustrating the pusher in a proximal position;

FIG. 5A is an enlarged view of an alternate embodiment of the anvil assembly and clip;

FIG. 6 is a cross-sectional view of the handle assembly, illustrating the levers in an approximated configuration;

FIG. 7 is an enlarged cross-sectional view of the anvil assembly, illustrating the pusher in a distal position, crimping closed the clips supported by the anvil;

FIG. 8 is a top view, in reduced scale, of a surgical retractor placed on a patient's chest to provide access to the heart;

FIG. 9 is an enlarged top view of the anvil assembly, illustrating the insertion of the harvested vessel into a passage therein;

FIG. 10 is an enlarged top view of the anvil assembly, illustrating the eversion of the harvested vessel about the anvil and the clips held thereby;

FIG. 11 is a top view of the surgical instrument with the harvested vessel mounted therein;

FIG. 12 is an enlarged perspective view of the harvested vessel everted on the anvil assembly positioned adjacent a slit in the coronary artery;

FIG. 13 is an enlarged perspective view in partial cross-section illustrating the anvil assembly and everted harvested vessel partially inserted within the coronary artery;

FIG. 14 is a cross-sectional view of the anvil assembly in the configuration of FIG. 5, illustrating the vascular tissue positioned adjacent the open clips;

FIG. 15 is a cross-sectional view of the anvil assembly in the configuration of FIG. 7, illustrating the vascular tissue within the crimped clips;

FIG. 16 is an enlarged perspective view of the anvil assembly in an open configuration to release the harvested vessel subsequent to the anastomosis;

FIG. 17 is an enlarged top view of the heart, illustrating the completed graft of the harvested vessel to the coronary artery.

DETAILED DESCRIPTION OF PREFERRED EMBODIMENTS

Figure 18:
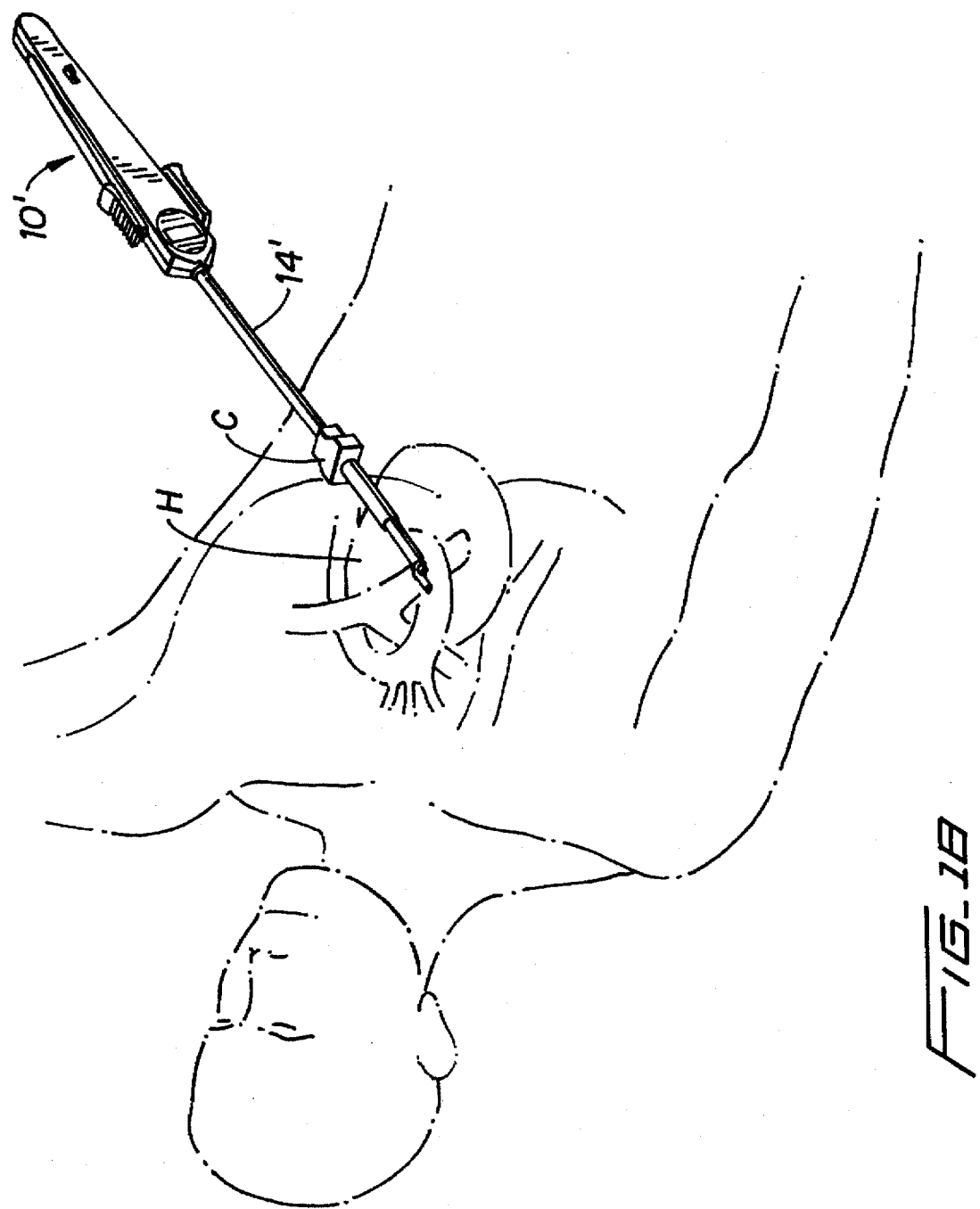
FIG. 18 is a side view showing insertion of an endoscopic version of the surgical instrument of FIG. 1 through a cannula.

The preferred embodiments of the apparatus and method disclosed herein will be discussed in terms of minimally invasive vascular grafts to the coronary artery. However, the subject apparatus may also find use in performing anastomosis of other tubular or luminal body structures.

In the drawings and in the description which follows, the term "proximal," as is traditional, will refer to the end of the apparatus which is closer to the operator, while the term "distal" will refer to the end which is further from the operator.

Referring now in detail to the drawings in which like reference numerals identify similar or identical elements, a first embodiment of the subject disclosure is illustrated in FIG. 1, and is designated generally by reference numeral 10. Surgical instrument 10 includes handle assembly 12, body portion 14, and anvil assembly 16. Surgical instrument 10 is configured to receive a harvested vessel, e.g. the internal mammary artery (IMA), through passage 18 in anvil assembly 16. The IMA is everted and joined to a coronary artery (not shown) by applying a series of non-penetrating clips thereto. The clips, which are supported on anvil assembly 16, are deformed simultaneously by actuation of the handle assembly 12 as will be described in greater detail below. The clips secure the vascular tissue without piercing it. Anvil assembly 16 is configured to release the IMA subsequent to the anastomosis.

Handle assembly 12 includes lock knob 20 positioned on housing or frame 22 configured to remotely secure anvil assembly 16 in a locked configuration surrounding the IMA. Lock knob 20 is illustrated in FIG. 1 in a first, proximal position corresponding to an unlocked configuration of anvil assembly 16. Handle assembly 12 also includes a pair of levers 24a and 24b mounted on frame 22 to advance a fastener closing (camming) member or pusher 26 and thereby close clips supported on fastener supporting member or anvil 28 to secure tissue held at anvil assembly 16. It is also contemplated that anvil 28 is movable with respect to pusher 26.

Turning now to FIG. 2, anvil assembly 16 includes a fastener support or anvil 28 and a fastener camming (forming) member or pusher 26. Since anvil 28 is configured to receive the IMA or other harvested vessel through passage 18, anvil 28 and pusher 26 are preferably laterally offset from body portion 14. Anvil 28 and pusher 26 define a longitudinal axis substantially parallel to the longitudinal axis of body portion 14. The distal end portion of anvil 28 includes a plurality of longitudinal channels 30 configured to support a plurality of "C"-shaped surgical fasteners or clips 32 held therein by friction or compression of the anvil and pusher. Clips 32 are radially aligned about anvil 28 (See, FIG. 2A). The distal portion of pusher 26 has a plurality of longitudinally aligned camming members 33 which are slidable within channels 30. Camming members 33 close clips 32 upon distal advancement of pusher 26. As will be described below, anvil 28 and pusher 26 are each composed of two halves that are pivotably secured by pivot pins 37 and 36, respectively (See, e.g. FIG. 3A). Locking pin 38 (illustrated in phantom) is actuated by lock knob 20. When locking pin 38 is disposed in a proximal position, each of two halves of anvil 28 and pusher 26 are freely pivotable about respective pivot pins 37 and 36.

Lock knob 20 can be moved to a second, distal position with respect to frame 22, indicated by the arrow in FIG. 1. Locking pin 38 is moved distally by lock knob 20 and passes through bore 40 in pusher 26, thereby maintaining both pusher 26 and anvil 28 (which is surrounded by pusher 26) in the closed and locked configuration.

FIGS. 3–3A illustrate the components of surgical instrument 10. As illustrated in FIG. 3, frame 22 includes left and right housing portions 42a and 42b respectively, in which the components of handle portion 12 are positioned. Housing portions are secured together by sonic welding or other known means. Levers 24a and 24b are mounted to housing portions 42a and 42b by pin 44 which permits pivotal motion of each of levers 24a and 24b with respect to frame 22.

The distal portion of levers 24a and 24b are secured to linkage 46 which consists of slide 48 and links 50a and 50b. Each of links 50a and 50b has a first end pivotably connected to levers 24a and 24b respectively, by pins 52a and 52b. A second end of each of links 50a and 50b is pivotably mounted to slide 48, such that relative movement of levers 24a and 24b about pin 44 will cause slide 48 to move longitudinally in channel 54 integrally formed in housing portions 42a and 42b. More particularly, approximation of levers 24a and 24b will displace slide 48 distally, while spacing of levers 24a and 24b will displace slide 48 proximally. A spring or other biasing element (not shown) may be interposed between levers 24a and 24b to normally bias levers 24a and 24b apart and thereby bias slide 48 in a proximal position.

Elongated body 14 includes a plurality of generally coaxial elements including outer sleeve 56, drive sleeve 58 and locking bar 60. Outer sleeve 56 is mounted adjacent the distal end portion of frame 22. In particular, the proximal end portion of outer sleeve 56 is secured by pins 64a and 64b positioned within adapter 62, which, in turn, is disposed within recess 66 in housing portions 42a and 42b. The distal end portion of outer sleeve 56 supports anvil assembly 16.

Drive sleeve 58 is coaxially slidable within outer sleeve 56. The proximal end portion of drive sleeve 58 is fixedly secured to slide 48 and is longitudinally slidable therewith in response to actuation of levers 24a and 24b. The distal end potion of drive sleeve 58 is mounted to pusher 26, as will be described in greater detail below.

An ejector tube may optionally be provided to assist in ejection of the fasteners from the anvil. The ejector tube may be moved proximally to cam the clip out from the anvil.

Locking bar 60 is coaxially slidable within drive sleeve 58. The proximal end portion of locking bar 60 is connected to lock knob 20 by pin 68 extending through openings 61. Lock knob 20 is longitudinally slidable within channel 70 formed in housing portions 42a and 42b. Tab 72 of lock knob 20 protrudes axially through window 74 defined in housing portion 42b to facilitate actuation by the surgeon. The distal end portion of locking bar 60 supports locking pin 38, which preferably has a smaller diameter than locking bar 60 and is axially offset therefrom (See Also, FIG. 2). Longitudinal movement of lock knob 20 facilitates the locking and unlocking of anvil assembly 16 as will be described below.

Turning now to FIG. 3A, the components of anvil assembly 16 are separable for release of a harvested vessel subsequent to anastomosis. In the orientation illustrated, anvil 28 consists of an upper portion 78a and a lower portion 78b. Upper portion 78a includes collar 80 for mounting to outer sleeve 56 (not shown). Collar 80 further defines bore 82 through which various components are inserted. Upper portion 78a and lower portion 78b each define a bore 84 and 86 respectively, through which pivot pin 37 is inserted to facilitate relative pivoting of portions 78a and 78b. As discussed above, portions 78a and 78b together define a passage 18 through which the harvested vessel may pass. Each of surgical fasteners 32 has a crown portion 94 configured to be received in longitudinal channel 30 and a pair of legs 96a and 96b having rounded, atraumatic tips 98a and 98b. Legs 96a and 96b are radially disposed along the outer periphery of anvil 28 adjacent the distal edge or lip 29. Lip 29 is disposed at an angle a with respect to the longitudinal axis of anvil 28 in order to provide the proper angle for the anastomosis of the IMA into the LAD (See, e.g, FIG. 5). Angle a is preferably between 30° and 60° in order to improve blood flow from the IMA into the LAD, and may reduce the risk of embolism. Crown portions 94 are generally aligned with the longitudinal axis of anvil 28. Legs 96a and 96b extend radially outwardly from anvil 28, and at least a portion of leg 96a extends proximally from anvil 28.

In the illustrated orientation, pusher 26 includes upper pusher portion 100a and lower pusher portion 100b mounted proximal of anvil 28. The distal end portion of drive sleeve 58 passes through bore 82 in anvil 28 and is connected to clevis portion 102 of upper pusher portion 100a, and is longitudinally movable therewith in response to actuation of levers 24a and 24b. Spaced apart shackles 104a and 104b receive shackle 106 of lower pusher portion 100b. Flange 104e fits into drive sleeve 58. Pivot pin 36 passes through bores 110a and 110b of shackles 104a and 104b respectively, and bore 112 of shackle 106 to permit pivotal movement of lower pusher portion 100b with respect to upper pusher portion 100a. As described above, a plurality of longitudinally aligned camming members 33 extend from pusher portions 100a and 100b. A distal camming surface 34 is defined at the distal end portion of each of camming members 33 to close clips 32 by camming legs 96b as will be described below. An interior portion of each of camming members 33 includes angled guides 39 which are slidable within longitudinal channels 30.

Upper pusher portion 100a and lower pusher portion 100b of movable pusher 26 are remotely locked in the closed position by locking pin 38 passing through bores 40a and 40b in upper pusher portion 100a and bore 118 in lower pusher portion 100b. Locking pin 38 has a rounded end 120 to facilitate passage of locking pin 38 through bores 40a, 40b, and 118.

Movable levers 24a and 24b are initially disposed in a spaced apart configuration. Slide 48 is positioned in a proximal position (FIG. 4) within channel 54, in a slightly "over-center" configuration with respect to links 50a, 50b. Drive sleeve 58 is disposed proximally with respect to outer sleeve 56. Passage 18 is laterally offset from body portion 14 (See, e.g. FIG. 2A). When locking pin 38 is disposed in bores 40a, 40b and 118, pusher 26 surrounds anvil 28 and maintains it in a closed configuration as well.

The orientation of pusher 26 with respect to anvil 28 shown in FIG. 5 corresponds to the spaced apart configuration of levers 24a and 24b of FIG. 4. Pusher 26 is positioned in a proximal position with respect to anvil 28. Camming surfaces 34 are disposed adjacent clips 32 in their initial, undeformed position.

Approximation of levers 24a and 24b remotely actuates pusher 26. Given the initially "over-center" position of slide 48, moving levers 24a and 24b together moves slide 48 distally through motion of links 50a and 50b. Slide 48 moves drive sleeve 58 distally as indicated by the arrow in FIG. 6.

Distal advancement of drive sleeve 56 (not shown) advances pusher 26 towards clips 32. Curved camming surfaces 34 of camming members 33 initially contact legs 96b of clips 32. As shown in FIG. 7, further distal movement of camming surfaces 34 simultaneously cam clips 32 into closed position by deforming crown 94 and approximating legs 96a and 96b. Clips 32 are not flattened by this camming process; legs 96a and 96b retain a relatively curved configuration as shown as they retain the vessel portions within the crimped legs without penetrating the vessel. Alternatively, anvil 28 is slidably mounted and moved proximally with respect to pusher 26 in order to crimp clips 32.

FIG. 5A illustrates an alternate embodiment of the clip and anvil assembly. Clip 132 has a pair of notches 132a, 132b for holding the clip rather than the frictional engagement of FIG. 5. Camming member 133a has a projecting distal camming surface 134a which engages notch 132a and is advanced in the same manner as camming member 133 of FIG. 4. Lip 29a has a projecting surface 29b which engages notch 132b.

An example of the clips which can be used are disclosed in Application Ser. No. 08/311,049, filed Sep. 23, 1994, the contents of which are incorporated herein by reference.

Operation of the Instrument

Turning now to FIGS. 8–18, the operation of surgical instrument 10 will now be described. Surgical instrument 10 may be used in conventional open CABG procedures using a median sternotomy or other large incision without stopping the heart. Alternatively, the thoracic "window" procedure may be used to achieve access. The "window" approach involves a smaller incision and less displacement of the ribs, and therefore is less traumatic to the patient. For this approach, conventional surgical techniques are used to determine the location of the incision I accessing chest cavity C. A surgical retractor, such as surgical retractor SR is used to access the heart and coronary arteries by creating the "window". Base B is placed on the chest of the patient with the opening of base B overlying the operative site. Incision I is made, exposing several ribs $R_3$, $R_4$, $R_5$, $R_6$.

Retractor assemblies RA are mounted to base B at various locations. Each of retractor assemblies RA includes blade BL having a hook to engage a rib therewith. Blade BL is positioned around a rib, which is deflected and retracted by moving blade BL radially outward. Additional retractor assemblies RA are mounted and used to retract ribs until a sufficiently large opening O in chest cavity C is defined to provide access to the heart. For example, sternum S and fourth rib $R_4$ and fifth rib $R_5$ can be spread apart to create a window. Alternatively, fourth rib $R_4$ and fifth rib $R_5$ are cut from sternum S and spaced to create a larger window as shown in FIG. 8. Alternatively, a fifth rib $R_5$ can be cut, and sternum S and fourth rib $R_4$ and sixth rib $R_6$ are spread. Base B is at least partially held in position over the operative site by tension created in retracting the ribs by retractor blades BL.

The internal mammary artery IMA is dissected from surrounding cartilage and muscle, and a free end is exposed. The coronary artery, e.g. the left anterior descending artery LAD, is then prepared for receiving IMA graft. The heart H is positioned either by traction sutures passing through the pericardium or by manipulation instruments which are held by surgical personnel or clamped to the operating table or to base B. Blood flow through the LAD can be restricted by cardiopulmonary bypass and pericardial cooling. Alternatively, a damping instrument may be applied directly on the LAD to restrict blood flow and reduce movement of the heart near the LAD.

The IMA is prepared for grafting to the LAD. Pusher 26 and anvil 28 are locked by advancement of locking pin 38. A free end of the IMA is inserted through passage 18 in anvil 28, such that the end of the IMA protrudes beyond the distal end portion of anvil 28 as shown in FIG. 9. Alternatively, the IMA may be inserted into anvil 28 prior to locking anvil assembly 16.

Next, as shown in FIG. 10, the free end of the IMA is everted around the lip portion 29 of anvil 28. In particular, tweezers T may be used to manually evert the IMA. Alternatively, a remotely actuated grasping instrument such as ENDO-GRASP instrument manufactured by United States Surgical Corporation of Norwalk, Conn., may be used. The IMA is grasped and stretched over collet portions 78a and 78b (not shown). The IMA engaged by legs 96a of clips 32 to hold the vessel in place. Care should be exercised to insure that the IMA has been engaged by each of legs 96a. The elasticity of the IMA provides a compression about anvil 28 in the everted configuration.

FIG. 11 illustrates the LAD prepared to receive the IMA. An incision $I_L$ is made in the LAD downstream from the occlusion. Surgical instrument 10 is manipulated such that anvil assembly 16 carrying the everted IMA is approximated with incision $I_L$ in the LAD.

The everted IMA is inserted into incision $I_L$ of the LAD (FIG. 12). The distal edge 29 of anvil 28 is configured with an angle in order to optimize the end-to-side anastomosis and to facilitate blood flow across the graft from the IMA to the LAD. This junction creates "heel" H and "toe" T portions in which an acute or obtuse angle between the vessels is defined.

Turning to FIG. 13, the distal end portion of tubular anvil 28 including everted IMA and clips 32 are inserted into incision $I_L$ in the LAD. The radial orientation of legs 96a and their atraumatic tips permits clips 32 to be inserted atraumatically into the LAD. Elasticity of the LAD closes incision $I_L$ about anvil 28.

Upon insertion, the surgeon retracts anvil assembly 16 to apply proximal force to surgical instrument 10. Such force permits the side wall of the LAD surrounding incision $I_L$ to be positioned between legs 96a and 96b of clips 32 (FIG. 14). By retracting anvil assembly 16, incision $I_L$ is forced to assume a circular shape corresponding to the circular cross-section of anvil 28 and makes uniform contact with the everted section of IMA. The LAD is also partially everted as shown. The symmetrical nature of the circular junction of IMA and LAD permits the consistent joining of the vessels about anvil 28, including "heel" H and "toe" T. Distal advancement of camming surfaces 34 of camming members 33 forms clips 32 about the IMA and LAD (FIG. 15). As can be appreciated, the IMA and LAD are clipped in intima to intima contact The LAD and IMA are securely compressed between legs 96a and 96b without piercing either vessel.

After the surgeon ascertains that a complete graft has been performed and that all of clips 32 have been properly formed, the surgeon may then release anvil assembly 16 from the IMA as described above by withdrawing locking pin 38 proximally from bores 40a, 40b, and 118 of pusher 26. Lower pusher portion 100b of pusher 26 is permitted to pivot open with respect to upper pusher portion 100a. This permits lower collet portion 78b to open, thereby freeing the IMA from anvil assembly 16 as shown in FIG. 16.

As illustrated in FIG. 17, the completed graft permits increased blood flow downstream from the occlusion. Any clamps on the IMA may be removed. If cardiopulmonary bypass is used, it is gradually removed. Alternatively, a clamp used on the coronary artery to restrict blood flow is removed and normal blood flow is permitted to resume.

Surgical instrument 10 may also have particular use for example in minimally invasive CABG procedures such as thoracoscopic procedures for grafting the IMA to the LAD, etc. As shown in FIG. 18, instrument 10' is provided with body portion 14' configured and dimensioned to be inserted through cannula C placed between the ribs. A thoracoscope (not shown) is likewise inserted through a second cannula in order to illuminate and visualize the procedure. It should be noted that use of the aforedescribed instruments in other procedures is also contemplated.

It will be understood that various modifications may be made to the embodiments shown here. For example, the instruments may be sized to perform anastomosis for other vessels and luminal tissue. Therefore, the above description should not be construed as limiting, but merely as exemplifications of preferred embodiments. Those skilled in the art will envision other modifications within the scope and spirit of the claims appended hereto.

What is claimed is:

1. A surgical instrument for anastomosis of first and second blood vessels, which comprises:
   a) a handle;
   b) a body portion extending distally from the handle;
   c) a fastener support mounted adjacent a distal end portion of the body portion;
   d) a plurality of surgical fasteners releasably supported by the fastener support, each surgical fastener having a leg with an atraumatic tip portion; and
   e) a fastener pusher mounted adjacent the fastener support, the fastener pusher and fastener support being relatively slidable in response to actuation by the handle to simultaneously deform the surgical fasteners to secure a first vessel and second vessel without piercing the vessels.

2. A surgical instrument as recited in claim 1, wherein the fastener support defines a passage therethrough for the reception of an end of the first vessel.

3. A surgical instrument as recited in claim 2, wherein the fastener support defines a longitudinal axis and has a distal edge angularly disposed with respect to the longitudinal axis.

4. A surgical instrument as recited in claim 2, wherein the passage in the fastener support is laterally offset from the body portion.

5. A surgical instrument as recited in claim 4, wherein the fastener support defines a longitudinal axis and has a distal edge angularly disposed with respect to the longitudinal axis.

6. A surgical instrument as recited in claim 5, wherein the fastener support is composed of at least two components.

7. A surgical instrument as recited in claim 5, wherein the fastener pusher is received in a notch formed in the fastener.

8. A surgical instrument as recited in claim 6, which further comprises:
   a lock remotely actuated adjacent the handle to secure together the components of the anvil.

9. A surgical instrument as recited in claim 1, wherein the passage in the fastener support is laterally offset from the body portion.

10. A surgical instrument as recited in claim 1, wherein the fastener support defines a longitudinal axis and has a distal edge angularly disposed with respect to the longitudinal axis.

11. A surgical instrument for anastomosis of first and second blood vessels, which comprises:
    a) a handle;
    b) a body portion extending distally from the handle;
    c) a fastener support mounted adjacent a distal end portion of the body portion;
    d) a plurality of surgical fasteners radially oriented about the fastener support and releasably supported thereby, each surgical fastener having a leg with an atraumatic tip portion; and
    e) a fastener pusher mounted adjacent the fastener support, the fastener pusher and fastener support being relatively slidable in response to actuation by the handle to simultaneously deform the surgical fasteners to secure a first vessel and second vessel without piercing the vessels.

12. A surgical instrument as recited in claim 11, wherein the fastener support defines a passage therethrough for the reception of an end of the first vessel.

13. A surgical instrument as recited in claim 12, wherein the passage in the fastener support is laterally offset from the body portion.

14. A surgical instrument as recited in claim 13, wherein the fastener support defines a longitudinal axis and has a distal edge angularly disposed with respect to the longitudinal axis.

15. A surgical instrument as recited in claim 11, wherein the fastener support and the fastener pusher are composed of at least two components.

16. A surgical instrument as recited in claim 15, which further comprises:

a lock remotely actuated adjacent the handle to secure together the components.

17. A method for anastomosis of first and second blood vessels, which comprises:

a) providing a surgical instrument having a fastener support defining a passage therethrough for reception of a first vessel, a plurality of surgical fasteners having at least one leg with an atraumatic tip portion and releasably supported by the fastener support at a distal end thereof;

b) positioning an end of the first vessel through the passage and everting the vessel over a distal end of the fastener support adjacent the plurality of surgical fasteners;

c) engaging the first vessel with the surgical fasteners;

d) inserting the distal edge of the fastener support, mounting the end of the first vessel into an opening in a side wall of a second vessel;

e) engaging a side wall of the second vessel adjacent an opening with the surgical fasteners; and f) simultaneously deforming the leg of each surgical fastener by actuation of the handle to secure the first and second vessels together without piercing the first and second vessels.

18. A method as recited in claim 17, which further comprises:

releasing the first vessel from the fastener support.

19. A method as recited in claim 18, wherein the fastener support is composed of at least two separable components, and wherein the step of releasing the first vessel includes separating the components of the fastener support.

20. A method as recited in claim 19, wherein the surgical instrument has a lock remotely actuable adjacent the handle for securing the components of the fastener support, and wherein the step of releasing the first vessel includes remotely releasing the lock.

21. A method as recited in claim 17, which further comprises:

percutaneously inserting the surgical instrument to the operative site adjacent the first and second blood vessels.

22. A method as recited in claim 17, wherein the surgical instrument has a fastener pusher mounted adjacent the fastener support, the fastener support and the fastener pusher being relatively slidable in response to the actuation of the handle, and wherein the step of simultaneously deforming the leg of each surgical fastener includes sliding the fastener pusher and the fastener support with respect to one another.

* * * * *